United States Patent
Harvie

(10) Patent No.: US 7,135,012 B2
(45) Date of Patent: *Nov. 14, 2006

(54) AUTOMATIC SELF CLEANING BLADDER RELIEF SYSTEM

(76) Inventor: Mark R. Harvie, 1150 Airport Dr., South Burlington, VT (US) 05403

(*) Notice: Subject to any disclaimer, the term of this patent is extended or adjusted under 35 U.S.C. 154(b) by 195 days.

This patent is subject to a terminal disclaimer.

(21) Appl. No.: 10/885,355

(22) Filed: Jul. 6, 2004

(65) Prior Publication Data

US 2004/0243075 A1 Dec. 2, 2004

Related U.S. Application Data

(63) Continuation-in-part of application No. 10/418,852, filed on Apr. 18, 2003, now Pat. No. 6,918,899, which is a continuation-in-part of application No. 10/369,240, filed on Feb. 19, 2003, now Pat. No. 6,706,027.

(60) Provisional application No. 60/359,672, filed on Feb. 26, 2002.

(51) Int. Cl.
*A61M 1/00* (2006.01)
*A61F 5/44* (2006.01)

(52) U.S. Cl. ............... 604/347; 604/319; 604/326; 604/329; 604/355

(58) Field of Classification Search ............ 604/540, 604/544, 317–357; 4/144.1, 144.2, 144.3, 4/144.4; 128/849; 600/574, 578, 579
See application file for complete search history.

(56) References Cited

U.S. PATENT DOCUMENTS

| | | | | |
|---|---|---|---|---|
| 4,356,012 A * | 10/1982 | Hofstetter | ......... | 55/385.4 |
| 4,709,660 A * | 12/1987 | Hrushesky | ......... | 119/751 |
| 4,747,166 A * | 5/1988 | Kuntz | ......... | 4/144.1 |
| 5,267,363 A * | 12/1993 | Chaffee | ......... | 5/710 |
| 5,279,512 A * | 1/1994 | Manale | ......... | 446/217 |
| 5,342,583 A * | 8/1994 | Son | ......... | 422/107 |
| 5,558,654 A * | 9/1996 | Hardy | ......... | 604/322 |
| 5,848,443 A * | 12/1998 | Waugh | ......... | 4/458 |
| 5,911,222 A * | 6/1999 | Lawrence et al. | ......... | 600/574 |
| 6,443,939 B1* | 9/2002 | Oki et al. | ......... | 604/393 |
| 6,740,066 B1* | 5/2004 | Wolff et al. | ......... | 604/319 |
| 7,018,366 B1* | 3/2006 | Easter | ......... | 604/327 |
| 2002/0193762 A1* | 12/2002 | Suydam | ......... | 604/327 |
| 2006/0015080 A1* | 1/2006 | Mahnensmith | ......... | 604/327 |

FOREIGN PATENT DOCUMENTS

WO  WO 00/57784 A1 * 10/2000

* cited by examiner

Primary Examiner—Tatyana Zalukaeva
Assistant Examiner—Michael G. Bogart
(74) Attorney, Agent, or Firm—Eric R. Benson, Esq.

(57) ABSTRACT

This invention relates to an automatic or semi-automatic bladder relief system, specifically designed to increase the overall sanitation and comfort for users requiring a means to dispose of urine in the absence of sanitary facilities in situations such as aircraft pilots and incontinent individuals. This invention incorporates an inflatable urine collection means that may be deflated after use. The power unit incorporates a disposable battery that is integrated into a disposable urine storage bag. This invention also utilizes a disposable urine storage bag with an isolated cleaning fluid chamber with a directional valve and pump system automatically rinsing and sanitizing the pump, hoses, collection means and the user with a cleaning fluid stored in the cleaning fluid chamber of the disposable urine storage bag. The disposable urine storage bag contains absorbent polymer crystals absorbing the urine as it is deposited in the bag during use.

24 Claims, 13 Drawing Sheets

AUTOMATIC SELF CLEANING BLADDER RELIEF SYSTEM

CROSS REFERENCE TO RELATED APPLICATION

This Application is a Continuation-In-Part of the patent application U.S. Ser. No. 10/418,852, filed Apr. 18, 2003 now U.S. Pat. No. 6,918,899, which in turn is a Continuation-In-Part of patent application U.S. Ser. No. 10/369,240 filed Feb. 19, 2003 (now issued U.S. Pat. No. 6,706,027) and claiming priority from Provisional Patent Application No. 60/359,672 which was filed on Feb. 26, 2002.

BACKGROUND ART

The use of human urinary collection and disposal systems is known in the prior art. For example U.S. Pat. No. 4,886,508 (Washington, 1989) discloses a ladies' external catheter assembly, however this device does not use a vacuum pump for drainage or utilize a moisture sensor. Also U.S. Pat. No. 4,610,675 (Triunfol, 1986) teaches a device for collecting fluid discharged from female organs that is designed solely for incontinent women, not female aircrew members and the design includes a pad, vacuum pump and liquid sensor, however, the pad is more invasive because it is formed of plastic and has ridges to move the labia to an open position for free flow of liquid. The vacuum pump of the Triunfol patent is powered by an electrical outlet and does teach battery operation of these devices. In U.S. Pat. No. 5,662,631 (Marx, Sep. 2, 1997) a male external catheter assembly with vacuum retention is disclosed wherein a male external catheter attachment incorporates a vacuum or a means to produce reduced pressure to aid in installing and keeping the device in place. U.S. Pat. No. 5,499,977 (Marx, Mar. 19, 1996) teaches another form of male external catheter with vacuum assist utilizing a rubber bulb that functions as a vacuum. As such, the basic concept of bladder discharge collection systems and their use are disclosed.

There are no acceptable bladder relief systems for incontinent adults. Urinary incontinence affects more than 13 million Americans in community and institutional settings. Thirty-eight percent of non-institutionalized patients older than 60 years of age experienced urinary incontinence, and almost 50 percent of institutionalized patients. The annual costs of bladder control problems in the United States for people older than 65 years of age was estimated at $26.3 billion in 1995, or $3,565 per affected person. Many incontinent males use commercially available diapers, which cannot contain urine from multiple urinations, and become heavy and uncomfortable when wet.

While each of these prior art patents disclose bladder relief systems which fulfill their respective particular objectives and requirements, and are most likely quite functional for their intended purposes, it will be noticed that none of the prior art cited disclose an apparatus and/or method that allow a user the comfort of automatic operation and large volume capacity. As such, there apparently still exists the need for new and improved bladder relief system to maximize the benefits to the user and minimize the risks of injury from its use.

There is also no acceptable bladder relief system for male aircrew members flying extended flight operations in single or dual-seat fighter and reconnaissance aircraft that do not have toilet facilities. Male aircrew members use two types of bladder relief devices, "piddle pack" bag systems and uncomfortable external catheters with tubing. The entire procedure for using the piddle pack takes several minutes. During this procedure the pilot is significantly distracted from flying the aircraft, which can place both himself and his aircraft in danger. The current piddle pack bag system can also be dangerous to use if the pilot needs to eject from the aircraft while urinating. The optimum bladder relief system would allow the pilot to eject from the aircraft even while urinating, which would require it to be hands-free and at least semi-automatic. In this respect, the present invention disclosed herein substantially fulfills this need.

None of the prior art teaches a device that self cleans the urine pumping unit. The high concentration of urea and ammonia in decomposing urine is very destructive to pumps that are utilized to transport urine as well as the tubing and collection means utilized by these devices. Also, there is a long felt need in the art for a device that also rinses and sanitizes the exposed skin of the user after urination. Prolonged exposure to urine can cause irritation and possible infection. In this respect, the present invention disclosed herein substantially fulfills these needs as well.

A significant problem with the prior art devices that have self contained powering systems, such as rechargeable batteries, is that users often neglect to recharge the unit and when the unit is needed it fails to work because the batteries have not been recharged. Therefore there is a significant need in the art for a device that has a reliable power source that minimizes if not eliminates a failure of the unit because of user error or neglect to properly maintain the power system in a charged state. In this respect, the present invention disclosed herein substantially fulfills this need.

An automated or semi-automated bladder relief device is important not just for the aircrew member's comfort, health and safety, but also for the safety of the aircraft and squadron. The system will significantly reduce the pilot's distraction or downtime during bladder relief, which will improve pilot and aircraft safety.

Similarly, there is also no acceptable bladder relief system for female aircrew members flying extended flight operations in aircraft that do not have toilet facilities. Male aircrew members use two types of bladder relief devices, piddle pack bag systems and external catheters with tubing. Female aircrew members cannot use the catheter/tubing assemblies designed for males. Instead, most use commercially available adult diapers. These diapers have the following drawbacks:

1. Neither the Disposable Absorption Containment Device (DACD) developed by NASA nor commercially available diapers have the capacity to hold the 1000 cc of urine produced during some long duration flights.
2. High g maneuvers force the female aircrew member downward into the seat, displacing urine from the diaper and leaving the female to sit in a wet flight suit and seat for the duration of the flight.
3. Prolonged exposure to urine can cause skin irritation and may develop into more serious conditions such as ulcers.

In this respect, the present invention disclosed herein substantially corrects these problems and fulfills the need for such a device.

Lastly the present invention may also be effectively used by passengers in aircraft without toilet facilities, glider pilots, non-ambulatory patients, incontinent adults, astronauts, rescue workers in hazmat suits, and long-distance truckers and race car drivers.

DISCLOSURE OF THE INVENTION

In view of the foregoing limitations inherent in the known types of bladder relief systems now present in the prior art, the present invention provides an apparatus that has been designed to automatically or semi-automatically collect urine in an environmentally challenging setting in a sanitary, safe and comfortable manner which are improvements which are patently distinct over similar devices and methods which may already be patented or commercially available. As such, the general purpose of the present invention, which will be described subsequently in greater detail, is to provide a field designed apparatus and method of use that incorporates the present invention. There are many additional novel features directed to solving problems not addressed in the prior art.

To attain this the present invention generally comprises a secure gender specific leakproof urine collection means, a fluid sensing unit, a suction means, and a storage and disposal means.

Several objects and advantages of the present invention are:

unlike the prior art urinary collection and disposal systems the present invention provides an automated or semi-automated collection system with a large urinary storage capacity. Also, unlike prior art this invention does provide a comfortable collection system that requires no manipulation to utilize leaving the user's hand free for vital tasks;

one embodiment of the present invention also provides for an inflatable urine collection or depository means that provides for maximum comfort for the user by allowing the urine collection or depository means to be maintained in its deflated condition while not in use thus minimizing the bulk and discomfort of prior art urine collection or depository systems and yet providing an effective leak resistant urine collection or depository area for evacuation by a urine transport means when inflated;

in yet another embodiment of the inflatable urine collection or depository means, air cushion tubing surrounds an open cell foam as a failsafe measure in the event of a failure of the inflation pump, such that a user may slightly elevate their body allowing the air cushion tubing to decompress as the open cell foam takes on its decompressed shape and size once relieved of the user's body weight thereby forming an effective leak resistant urine collection or depository area for evacuation by a urine transport means when inflated;

also unlike prior art urine collection or depository means the inflatable embodiment of the present invention may have more than one air cushion tube in the event that another air cushion tube fails to inflate or ruptures;

in the most preferred embodiment this invention automatically detects the completion of urination and the pump mechanism reverses itself closing the one way valve to its urine storage compartment in a disposable bag. By doing this the pump then draws a cleaning fluid from a cleaning fluid storage compartment in the disposable bag through the device and against the user effectively rinsing and sanitizing the user and the device and then the pump reverses itself once again and deposits the used cleaning fluid in the disposable urine storage bag.

another novel feature of the most preferred embodiment of this invention is the utilization of a disposable battery power system that is attached to the disposable bag. The disposable battery provides ample power to pump up to 1.6 liters of urine and sufficient cleaning fluid to effectively rinse and sanitize the user and the system and then deposit the used cleaning fluid into the storage bag. Prior art devices that utilized rechargeable battery packs were not only heavy and expensive, but in many applications user's often neglect to charge the unit effectively, or at all, and hence experience unit failure when they need it most.

In all embodiments of the invention the disposable urine bag utilizes super absorbent polymer crystals that have a gelling affect on the urine and may further have a urine deodorizer mixed within the crystals. To further eliminate odors from the invention it utilizes a charcoal air filter to filter the air that exits the disposable urine storage bag while in use.

the present invention also provides for ease of set up, use, urine storage and disposal; and the present invention also provides an advancement in ecological protection by eliminating the need for disposal of environmentally damaging and bulky diaper materials.

These together with other objects of the invention, along with the various features of novelty which characterize the invention, will be pointed out with particularity in the claims which will be annexed to and forming a part of the full patent application once filed. For a better understanding of the invention, its operating advantages and the specific objects attained by its uses, reference should be had to the accompanying drawings and descriptive matter in which there is illustrated preferred embodiments of the invention.

BEST MODES FOR CARRYING OUT THE INVENTION

I. Preferred Embodiments

Figure 1:
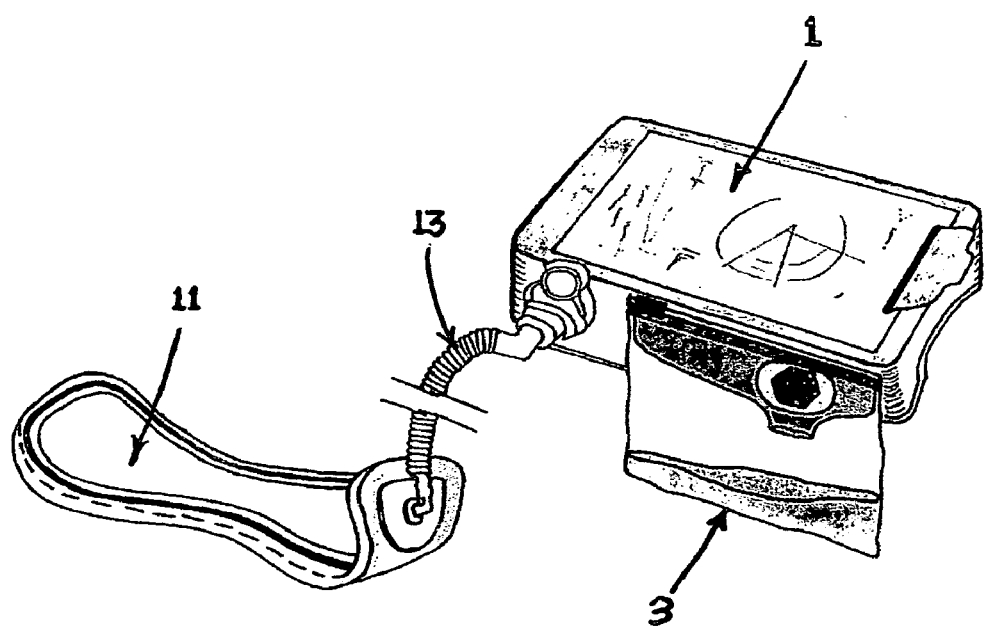
FIG. 1 is a perspective view of the female user embodiment.
Figure 1A:
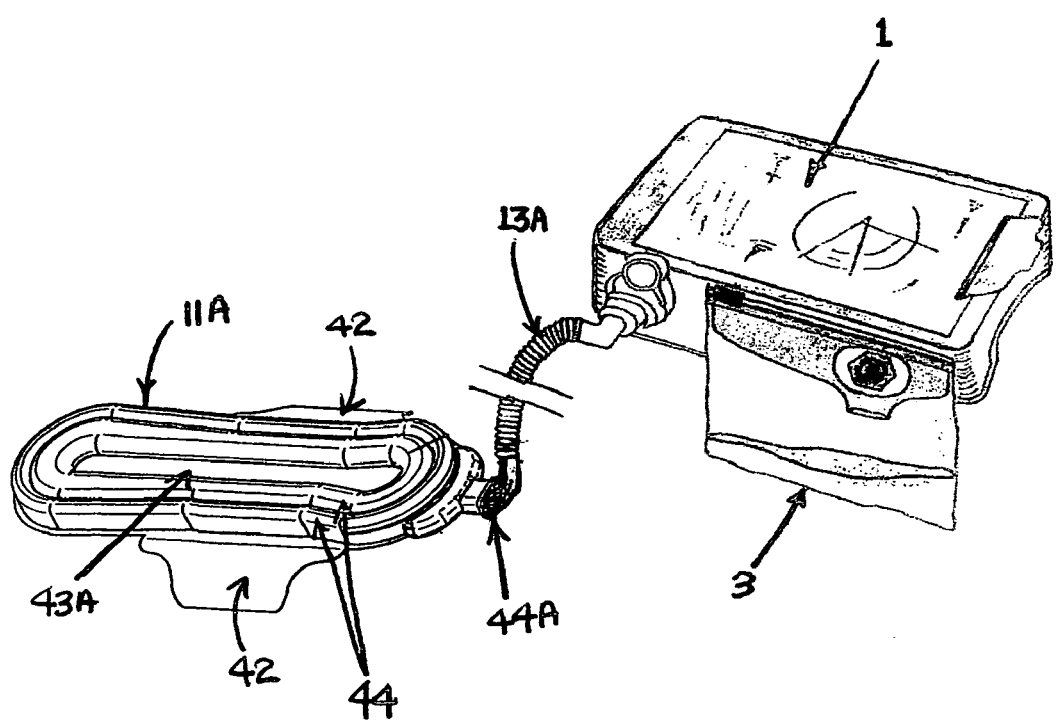
FIG. 1A is a perspective view of the female user embodiment utilizing the fully inflated inflatable embodiment of the female pad.
Figure 1B:
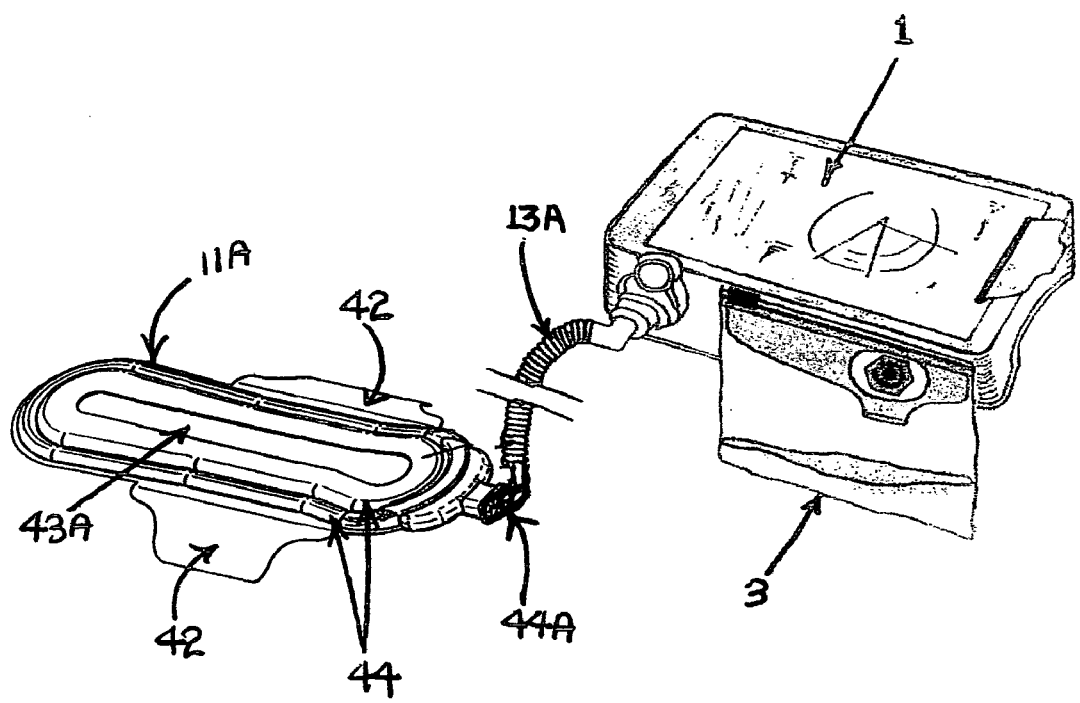
FIG. 1B is a perspective view of the female user embodiment utilizing the fully deflated inflatable embodiment of the female pad.
Figure 2:
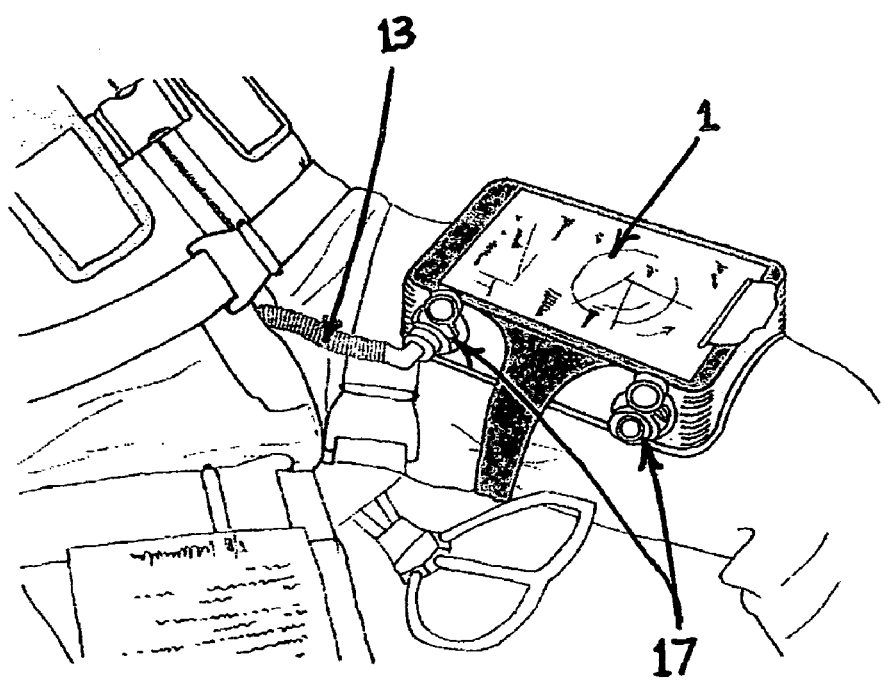
FIG. 2 is a perspective view of the invention attached to a user and in use.
Figure 3:
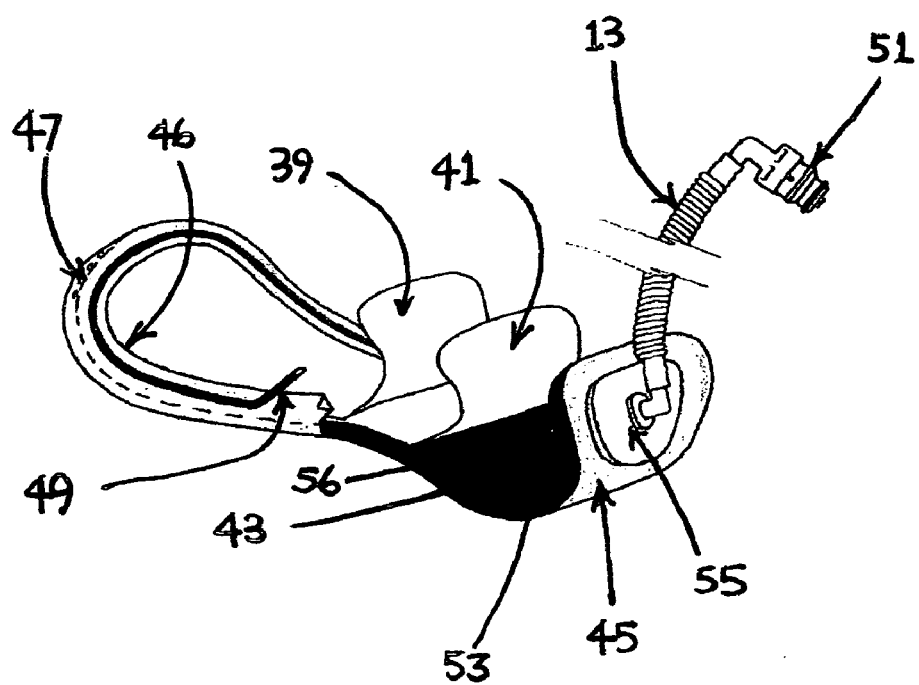
FIG. 3 is an expanded cut-away perspective view of the female pad of the female user embodiment depicted in FIG. 1.
Figure 3A:
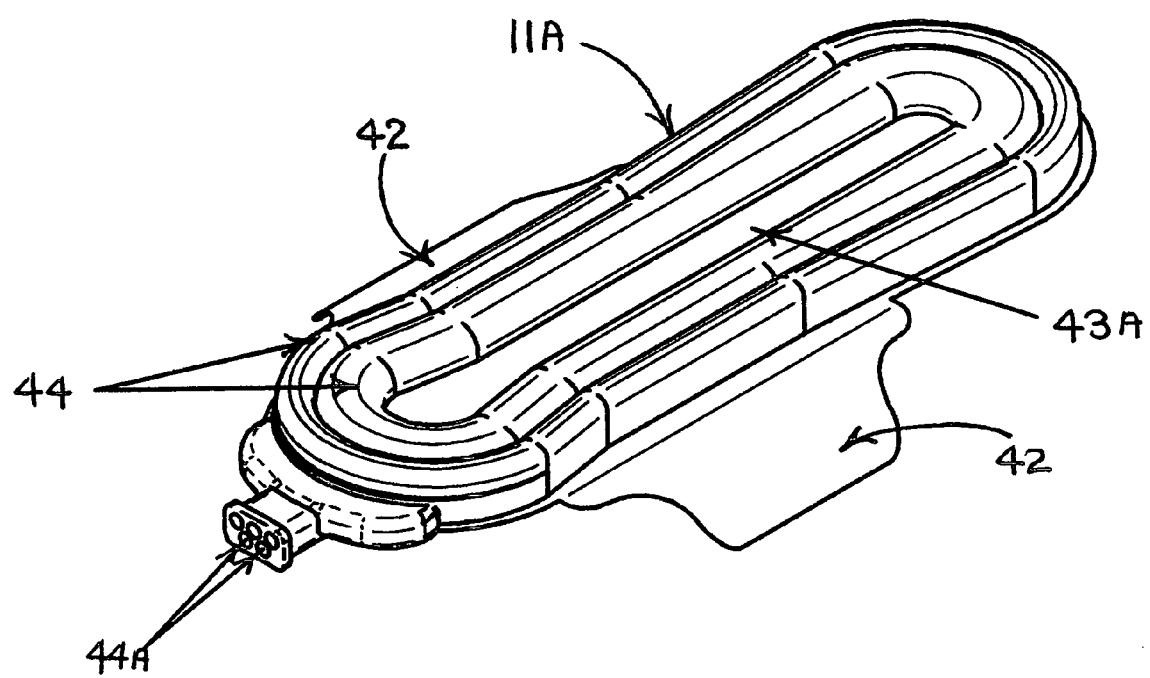
FIG. 3A is a perspective view of the inflatable embodiment of the female pad of the female user embodiment when fully inflated as depicted in FIG. 1A.
Figure 3B:
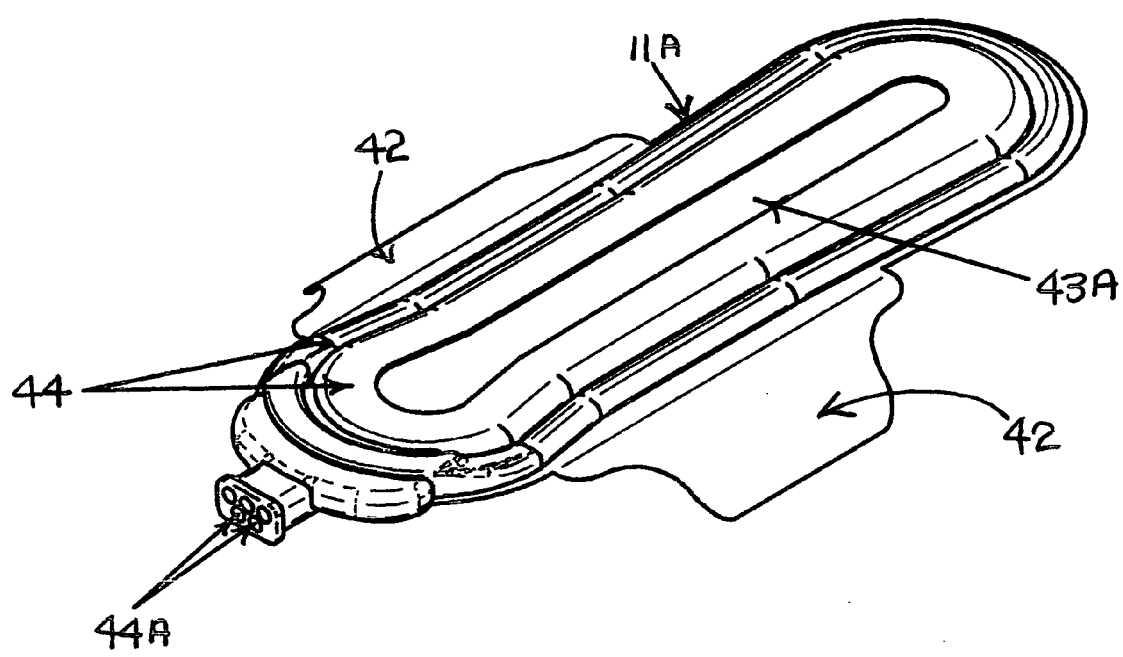
FIG. 3B is a perspective view of the inflatable embodiment of the female pad of the female user embodiment when fully deflated as depicted in FIG. 1B.
Figure 4:
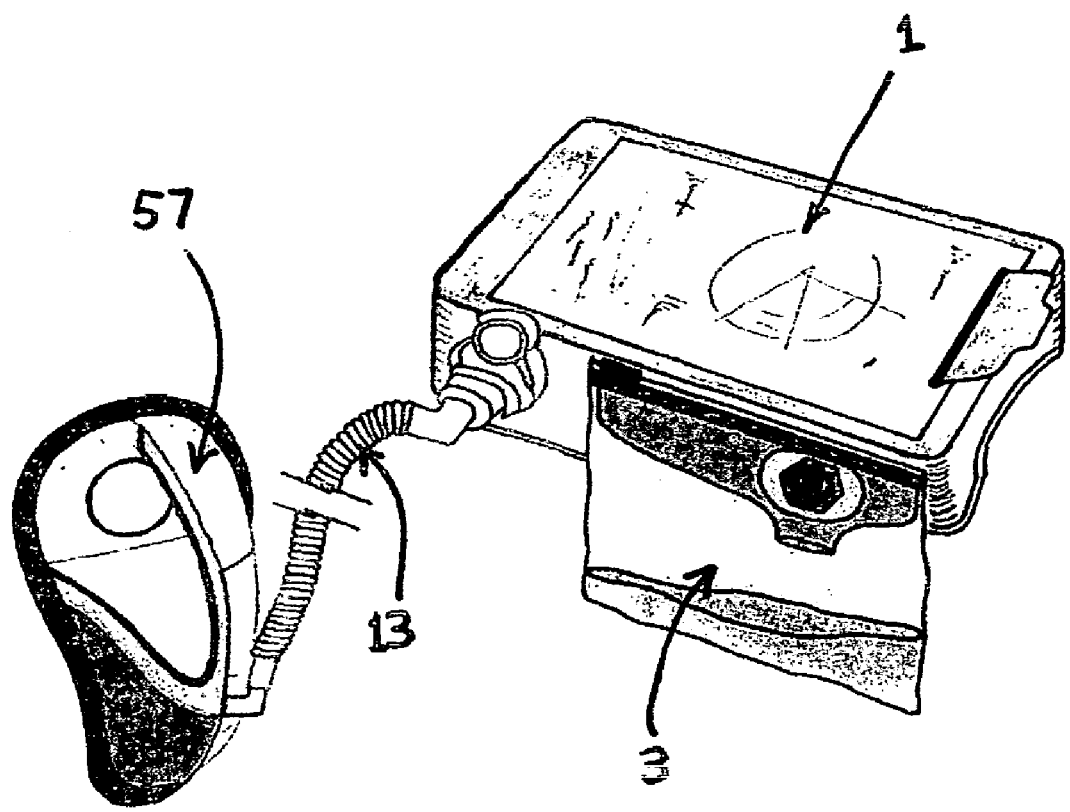
FIG. 4 is a perspective view of the male user embodiment.

With reference now to the drawings, and in particular to FIGS. 1–9 thereof, a new and novel apparatus for an automatic bladder relief system embodying the principles and concepts of the present invention and generally designated collectively comprising two main components in the female user embodiment by the reference numeral 1 and 11 in FIG. 1, and in the male user embodiment by the reference numeral 1 and 57 in FIG. 4.

List and Description of:

General Description of Reference Numerals in the Description and Drawings

Any actual dimensions listed are those of the preferred embodiment. Actual dimensions or exact hardware details and means may vary in a final product or most preferred embodiment and should be considered means for so as not to narrow the claims of the patent.

(1) Suction Control Unit
(1A) Air Pump
(2) Suction Vacuum Pump
(3) Urine Collection Bag
(5) DC Motor
(7) Rechargeable Battery Pack
(9) Recharge Circuitry
(11) Female Pad
(11A) Inflatable Female Pad
(13) Suction Hose
(13A) Combination Suction and Air Pressure Hose
(17) Quick-Disconnect Hose Couplings
(19) Power ON/OFF Button
(21) Timed Interval ON/OFF Button
(23) Vacuum Pump Impeller
(25) Filter
(27) Battery Pack
(29) LCD Status Display
(31) Flow Chamber
(33) Suction Control Unit Air/Liquid Inlet
(35) Suction Control Unit Liquid Outlet
(37) Suction Control Unit Air Exhaust Outlet
(39) Facing Layer (Female User Embodiment)
(39M) Facing Layer (Male User Embodiment)
(41) Wicking Layer (Female User Embodiment)
(41M) Wicking Layer (Male User Embodiment)
(42) Stability Wings
(43) Urine Collection Layer (Female User Embodiment)
(43A) Base Pad
(43M) Urine Collection Layer (Male User Embodiment)
(44) Air Cushion Tubing
(44A) Air Pressure Hose Connection
(45) Moisture-Proof Outer Layer (Female User Embodiment)
(45M) Moisture-Proof Outer Layer (Male User Embodiment)
(46) Outer Layer Wall (Female User Embodiment)
(46M) Outer Layer Wall (Male User Embodiment)
(47) One-Way Airflow Inlet Holes (Female User Embodiment)
(48) One-Way Airflow Inlet Holes (Male User Embodiment)
(49) Soft Sealing Strips
(50) Isolation Membrane
(51) Quick-Disconnect Plug
(52) Cup Front
(53) Inside Cup Area (Female User Embodiment)
(53M) Inside Cup Area (Male User Embodiment)
(55) Moisture Sensor
(56) Urine Cavity
(57) Male Cup
(58) Air Exit Hole
(59) Cleaning Fluid Compartment
(60) One Way Cleaning Fluid Valve
(61) Quick Connect Fluid and Electrical Connection
(62) Super Absorbent Polymer Crystals
(63) Urine Deodorizer
(64) One Way Flow Valve Into Urine Collection Bag
(65) Disposable Battery Pack
(66) Charcoal Air Filter Detailed Description of the Preferred Embodiments 1. Suction Control Unit The Suction Control Unit (1) is a re-usable piece of hardware containing a suction vacuum pump (2), DC motor (5), rechargeable battery pack (7) and recharge circuitry (9). A built-in, battery-powered suction vacuum pump (2) sucks the urine from the Male Cup (57) in the male user embodiment and Female Pad (11) of the female user embodiment through a suction hose (13) and deposits the collected fluid into a Urine Collection Bag (3). Quick-disconnect hose couplings (17) connect and disconnect the Urine Collection Bag (3) and suction hose (13) from the Suction Control Unit (1). The Suction Control Unit (1) has two modes of operation: one power "ON/OFF" button (19) and one button that turns the unit "ON" and then "OFF" after a timed interval (21). A small, high-power DC motor is used, similar to those used in cordless vacuum cleaners. The DC motor (5) spins the vacuum pump impeller (23) to provide the suction required to draw the urine from the urine cavity (56) of the Male Cup (57). The system uses a filter (25) of charcoal or other material to deodorize the exhaust air. In the preferred embodiment, a battery pack (27) of rechargeable Nickel-Metal Hydride (NIMH) batteries are used to provide the power supply for the DC motor (5). A two-digit LCD Status Display (29) with backlight indicates the amount of time remaining in the battery charge, and the number of bladder relieves left in the power supply charge. There are other power supplies available for other applications of this invention, from lithium batteries to 110-volt wall outlets. The recharge circuitry allows the battery pack to be plugged into a wall outlet for recharging without damaging the batteries.

A flow chamber (31) is contained in the Suction Control Unit (5). The flow chamber (31) begins at the Suction Control Unit Air/Liquid Inlet (33) and ends at both the Suction Control Unit Liquid Outlet (35) and the Suction Control Unit air exhaust outlet (37). This flow chamber (31) separates moisture from the vacuum airflow and channels the liquid to the Suction Control Unit Liquid Outlet (35) and the air to the Suction Control Unit Air Exhaust Outlet (37). The Suction Control Unit Air Exhaust Outlet (37) is fitted with a deodorizing air Filter (25).

2. Male Cup

Figure 5:
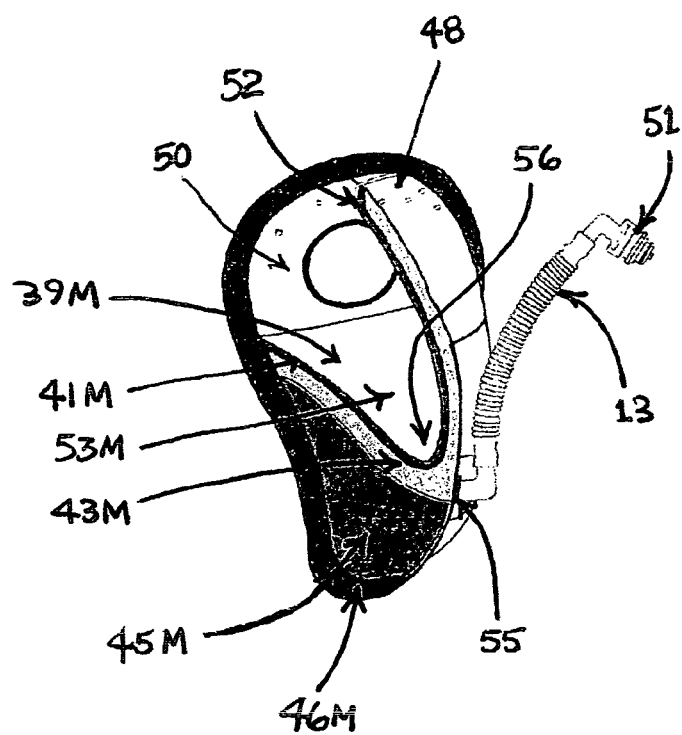
FIG. 5 is a cut-away perspective view of the male cup of the male user embodiment depicted in FIG. 4.
Figure 6:
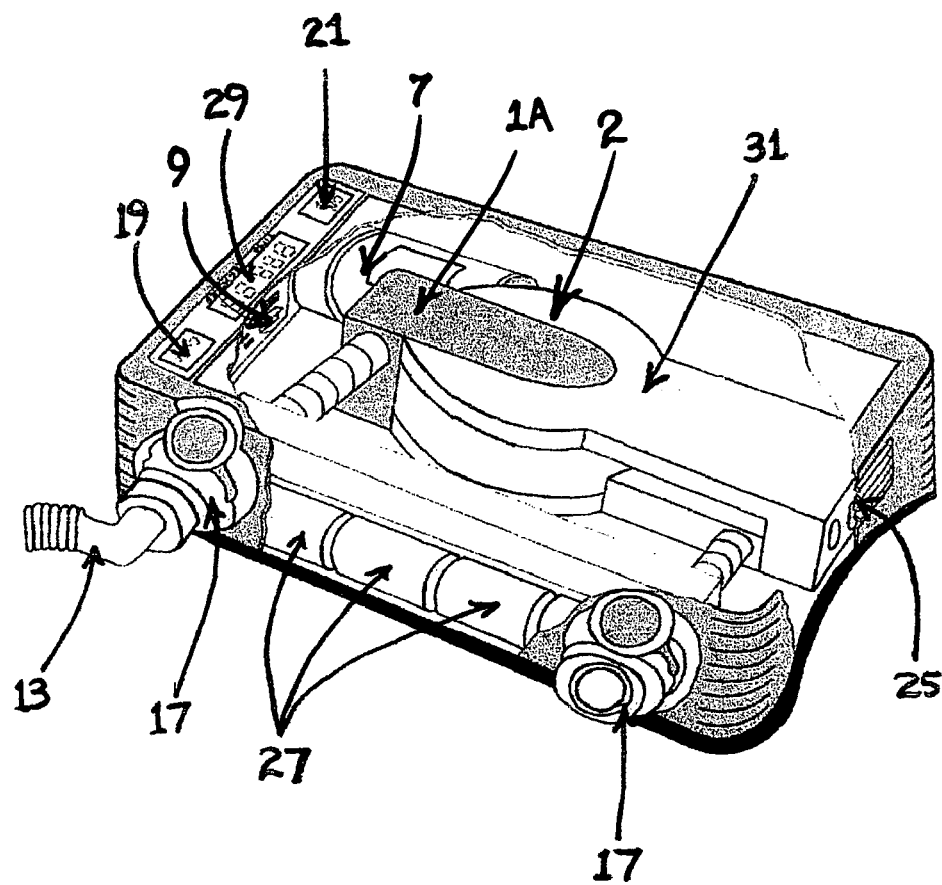
FIG. 6 is a cut-away perspective view of the suction control unit.
Figure 7:
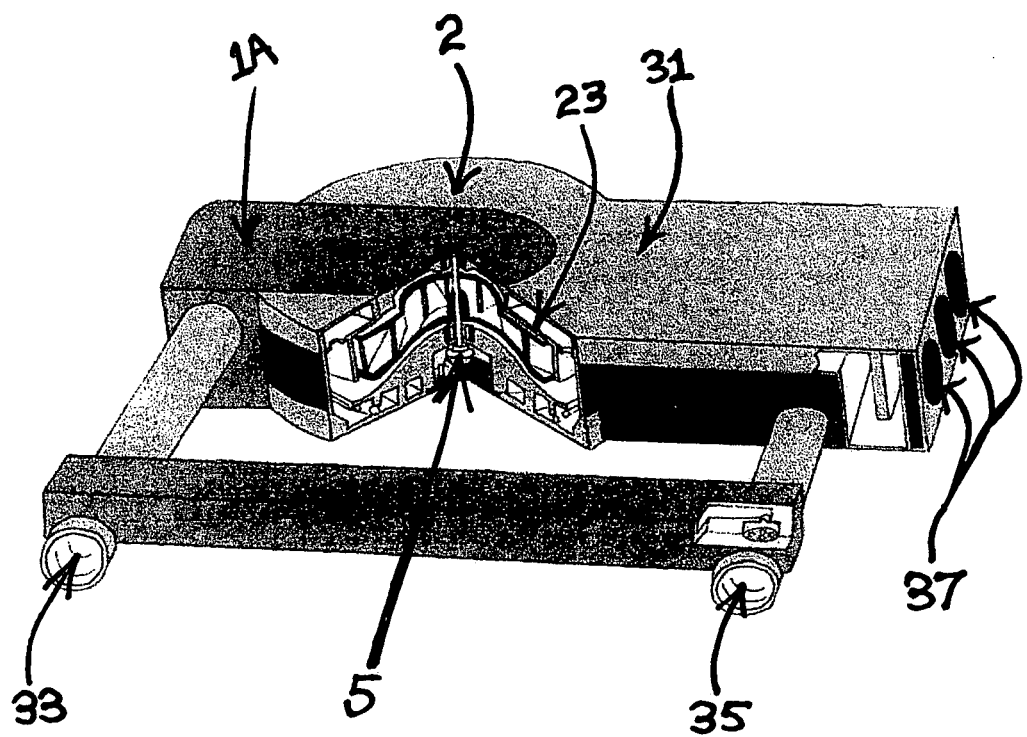
FIG. 7 is a cut-away perspective view of the flow chamber.

The Male Cup (57) is a disposable soft cup, approximately the same size and shape as a men's athletic protective cup. FIG. 5 shows a cut-away view of a Male Cup (37). The cup has four layers: a facing layer (39M), wicking layer (41M), urine collection layer (43M) and Moisture Proof Outer Layer (45M). The Moisture Proof Outer Layer (45M) is attached to and contains the facing layer (39M), wicking layer (41M), urine collection layer (43M) along the edges thereof by means of the Outer Layer Wall (46M). A Urine Cavity (56) is defined by the urine collection layer (43M) and the Moisture Proof Outer Layer (45M) in the inside cup area (53M). The facing layer (39M), which lies against the skin, is made of a soft, non-woven, non-absorbent polymer. The wicking layer (41M) is made of a woven polymer. It pulls moisture away from the facing layer (39M) and prevents it from going back through the facing layer (39M), much like a one-way fluid check valve. The urine collection layer (43M) is made of an open cell foam material or other material capable of collecting fluid, and provides a Urine Cavity (56) in its placement juxtaposed to the Moisture Proof Outer Layer (45M) for the vacuum suction airflow produced by the Suction Vacuum Pump (2) to suck fluids and moisture out of the Male Cup (57) and away from the body.

One-way airflow inlet holes (48) in the top of the Male Cup (57) facilitate the evacuation of liquids and provide air flow for drying the Male Cup's (57) layers. An isolation membrane (50) made of a thin, flexible material such as silicon rubber comfortably keeps a man's penis inside the Male Cup (57) compartment and prevents any leaking. The cup front (52) is made of a stretchable material such as silicon rubber that opens automatically to accommodate size changes.

The suction hose (13) at the front of the Male Cup (57) is connected to the Suction Control Unit (1). The Suction Control Unit (1) sucks all fluids from the Male Cup (57) through the suction hose (13) and deposits them into the Urine Collection Bag (3). In the preferred embodiment, the flexible, disposable suction hose (13) is outfitted with a quick-disconnect plug (51) on the end that connects to the Suction Control Unit (1). The suction hose (13) may be made of a convoluted, easily bendable material with spiral construction. This allows a smaller bending radius so that the suction hose (13) can be stowed in a person's clothing or flight suit while not in use, and permits all of the urine to drain out of the suction hose (13).

The Moisture-Proof Outer Layer (45M) of the Male Cup (57) is made of dense rubber to hold the Male Cup (57) in place. The Male Cup (57) is also held in place with a standard athletic jock strap. Most of the outer portion of the Male Cup (57) is constructed of soft rubber.

3. Urine Collection Bag in Male User Embodiment

The system is compatible with many types of Urine Collection Bags (3) including a disposable plastic bag containing super absorbent polymer crystals with a 500 cc urine capacity, and a larger, 1600 cc capacity Urine Collection Bag (3). Users who do not want to wear a Urine Collection Bag (3) for a long period of time can use smaller Urine Collection Bags (3). A zip lock top on the smaller Urine Collection Bags (3) allows its use as a standard piddle pack. Users who prefer not to change Urine Collection Bags (3) after each urination can wear a larger leg or pocket Urine Collection Bag (3). A quick-disconnect similar to the quick-disconnect plug (51) can also be built into the Urine Collection Bags (3) for easy attachment and replacement.

Use by Male Air Crew Members

The Suction Control Unit (1) can be packaged to double as a pilot's kneeboard as depicted in FIG. 2. The knee-board is molded and adjustable to fit the curve of the thigh. The aircrew member can carry the Suction Control Unit (1) in his helmet bag or wear it strapped to a thigh without giving the appearance of wearing bladder relief equipment. The quick-disconnect plug (51) hose couplings allow aircrew members to wait until they are seated in their aircraft or until they have to urinate to connect the Urine Collection Bag (3) and the suction hose (13) of the Male Cup (57) to the Suction Control Unit (1). The size and shape of the Urine Collection Bag (3) is designed to fit within the limited confines of the aircraft cockpit and navigator's seat. Piddle packs used by some male pilots are too long and difficult to open to its full length in a cockpit.

Use for Male Urinary Incontinence

Wheelchair users require a quieter, more discreet version of the Suction Control Unit (1) (i.e. with concealed hoses). The Suction Control Unit (1) can be mounted to the person's wheelchair and the hoses concealed under the person's clothing. Many urinary incontinent adults are not in wheelchairs, but are bedridden. A larger urine collection bag (3) that does not contain super-absorbent polymer can be attached to the Suction Control Unit (1) that can be emptied and reused. For ambulatory adults and children, a quiet Suction Control Unit (1) can be housed in a fanny pack that can also hold a concealed Urine Collection Bag (3).

Many urinary incontinent adults do not know in advance that they are about to urinate. It is therefore impractical to expect them to activate the Suction Control Unit (1) before urinating. Instead, a moisture sensor (55) is installed in the Male Cup (57) to automatically activate the Suction Control Unit (1) when moisture is sensed in the urine cavity (56).

4. Suction Control Unit in use with Female User Embodiment

The Suction Control Unit (1) is a reusable piece of hardware containing a suction vacuum pump (2), DC motor (5), rechargeable battery pack (7) and recharge circuitry (9). A built-in, battery-powered suction vacuum pump (2) sucks the urine from the Female Pad (11) through a suction hose (13) at the front of pad and deposits the urine into a Urine Collection Bag (3). Quick-disconnect hose couplings (17) connect and disconnect the Urine Collection Bag (3) and the suction hose (13) from the Suction Control Unit (1). The Suction Control Unit (1) has two modes of operation: one power "ON/OFF" button (19) and one button that turns the unit "ON" and then "OFF" after a timed interval (21).

A small, high-power DC motor (5) is used, similar to those used in cordless vacuum cleaners. The DC motor (5) spins the vacuum pump impeller (23) to provide the suction required to draw the urine from the Female Pad (11). The system uses a filter (25) of charcoal or other material to deodorize the exhaust air. In the preferred embodiment, a battery pack (27) of rechargeable Nickel-Metal Hydride (NIMH) batteries are used to provide the power supply for the DC motor. A two-digit LCD Status Display (29) with backlight indicates the amount of time remaining in the battery charge, and the number of bladder relieves left in the power supply charge. There are other power supplies available for other applications of this invention, from lithium batteries to 110-volt wall outlets. The recharge circuitry allows the battery pack (27) to be plugged into a wall outlet for recharging without damaging the batteries.

A flow chamber (31) is contained in the Suction Control Unit (1). The flow chamber (31) begins at the Suction Control Unit Air/Liquid Inlet (33) and ends at both the Suction Control Unit Liquid Outlet (35) and the Suction Control Unit Air Exhaust Outlet (37). This flow chamber (31) separates moisture from the vacuum airflow and channels the liquid to the Suction Control Unit Liquid Outlet (35) and the air to the Suction Control Unit Air Exhaust Outlet (37). The Suction Control Unit Air Exhaust Outlet (37) is fitted with a deodorizing air filter (25).

5. Female Pad

The Female Pad (11) is a disposable urine collection pad similar in size to a large feminine pad used for menstruation. FIG. 3 shows an expanded view of the Female Pad (11). The Female Pad (11) has four layers: a facing layer (39), wicking layer (41), urine collection layer (43) and moisture-proof outer layer (45). The Moisture Proof Outer Layer (45) is attached to and contains the facing layer (39), wicking layer (41), urine collection layer (43) along the edges thereof by means of the Outer Layer Wall (46). A Urine Cavity (56) is defined by the urine collection layer (43) and the Moisture Proof Outer Layer (45) in the inside cup area (53). The facing layer (39), which lies directly against the skin, is made of a soft, non-woven, non-absorbent polymer. The wicking layer (41) is made of a woven polymer. It pulls moisture away from the facing layer (39) and prevents it from going back through the facing layer (39), much like a one-way fluid check valve. The urine collection layer (43) is made of open cell foam or other material or other material capable of collecting fluid, and provides a Urine Cavity (56) in its placement juxtaposed to the Moisture Proof Outer Layer (45) for the vacuum suction airflow produced by the Suction Vacuum Pump (2) to suck fluids and moisture out of the Female Pad (11) and away from the body. The Moisture Proof Outer Layer (45), a moisture-proof barrier made of soft, flexible plastic, wraps around the sides of the Female Pad (11) to prevent side leakage.

One-way airflow inlet holes (47) in the back end of the Female Pad (11) facilitate the evacuation of liquids and provide air flow for drying the Female Pad's (11) layers. The Female Pad (11) has a contoured shape for a more comfortable and reliable fit. Soft sealing strips (49) around the Female Pad (11) face perimeter prevent side leaks. The Female Pad (11) is held in place with a comfortable but sturdy undergarment available in women's apparel stores.

The suction hose (13) at the front of the Female Pad (11) is connected to the Suction Control Unit (1). The Suction Control Unit (1) sucks all fluids from the Female Pad (11) through the suction hose (13) and deposits them into the Urine Collection Bag (3). In the preferred embodiment, the flexible, disposable suction hose (13) is outfitted with a quick-disconnect plug (51) on the end that connects to the Suction Control Unit (1). The suction hose (13) may be made of a convoluted, easily bendable material with spiral construction. This allows a smaller bending radius so that the suction hose (13) can be stowed in a person's clothing or flight suit while not in use, and permits all of the urine to drain out of the suction hose (13).

6. Urine Collection Bag in Female User Embodiment

The system is compatible with many types of Urine Collection Bags (3) including a disposable plastic bag containing super absorbent polymer crystals with a 500 cc urine capacity, and a larger, 1600 cc capacity bag. Users who do not want to wear a Urine Collection Bag (3) for a long period of time can use smaller Urine Collection Bags (3). Users who prefer not to change Urine Collection Bags (3) after each urination can wear a larger leg or pocket Urine Collection Bags (3). A quick-disconnect similar to the quick-disconnect plug (51) can also be built into the Urine Collection Bags (3) for easy attachment and replacement.

7. Inflatable Urine Collection Means Embodiment

As depicted in FIGS. 1A, 1B, 3A, & 3B the urine collection means of the present invention may also be made of a Base Pad (43A) to which is attached at least one inflatable Air Cushion Tubing (44) that are inflated by the user prior to urination by activation of the Air Pump (1A) that is housed inside Suction Control Unit (1). The activated Air Pump (1A) pumps air into one or more Air Cushion Tubing (44) through the air hose portion of the Combined Suction and Air Pressure Hose (13A) and is connected by the Air Pressure Hose Connection (44A), which Air Cushion Tubing (44) when inflated forms an area where discharged urine from the user may pool without contact with the user and then be transported by suction through the suction hose portion of the Combined Suction and Air Pressure Hose (13A) by the vacuum suction airflow produced by the Suction Vacuum Pump (2) of the Suction Control Unit (1) that suck fluids and moisture out of the Inflatable Female Pad (11A) and away from the user's body. The Suction Control Unit (1) then transports the suctioned urine into the Urine Collection Bag (3). After use the Air Pump (1A) is deactivated and the Air Cushion Tubing (44) deflates by means of compression brought on by the user's body weight after use returning the urine collection means to a flatter and more comfortable condition for the user. In its inflated condition the inflatable urine collection means provides a contained area for the pooling of the user's urine away from the body permitting the urine to be transported by the urine transport means and minimizing the opportunity for the urine to come in contact with the user's body or genital area. The Inflatable Female Pad (11A) has a contoured shape for a more comfortable and reliable fit. Stability Wings (42) attached to the sides of the Inflatable Female Pad (11A) serve to hold the Inflatable Female Pad (11A) in proper position on the user and prevent side leaks. The Inflatable Female Pad (11A) is held in place with a comfortable but sturdy undergarment available in women's apparel stores.

The Combination Suction and Air Pressure Hose (13A) at the front of the Inflatable Female Pad (11A) is connected to the Suction Control Unit (1). The Suction Control Unit (1) sucks all fluids from the Inflatable Female Pad (11A) through the Combination Suction and Air Pressure Hose (13A) and deposits them into the Urine Collection Bag (3). In the preferred embodiment, the flexible, disposable Combination Suction and Air Pressure Hose (13A) is outfitted with a connection means on the end that connects to the Air Pressure Hose Connection (44A). The Combination Suction and Air Pressure Hose (13A) may be made of a convoluted, easily bendable material with spiral construction. This allows a smaller bending radius so that the Combination Suction and Air Pressure Hose (13A) can be stowed in a person's clothing or flight suit while not in use, and permits all of the urine to drain out of the Combination Suction and Air Pressure Hose (13A).

In yet another embodiment the Air Cushion Tubing (44) contains an open cell foam as a failsafe measure in the event of a failure of the Air Pump (1A), such that a user may slightly elevate their body allowing the Air Cushion Tubing (44) to decompress as the open cell foam takes on its decompressed shape and size once relieved of the user's seated body weight thereby forming an effective leak resistant urine collection or depository area for evacuation by the urine transport means when inflated.

While not depicted, one ordinarily skilled in the art could apply this inflatable design to a cup designed to accommodate a male user and based upon the teaching of this invention such a male embodiment would be obvious.

Use by Female Air Crew Members

The Suction Control Unit (1) can be packaged to double as a pilot's kneeboard as depicted in FIG. 2. The kneeboard is molded and adjustable to fit the curve of the thigh. The aircrew member can carry the Suction Control Unit (1) in her helmet bag or wear it strapped to a thigh without giving the appearance of wearing bladder relief equipment. The quick-disconnect plug (51) suction hose (13) couplings allow aircrew members to wait until they are seated in their aircraft or until they have to urinate to connect the Urine Collection Bag (3) and the Female Pad (11) suction hose (13) to the Suction Control Unit (1). The size and shape of the Urine Collection Bag (13) is designed to fit within the limited confines of the aircraft cockpit and navigator's seat

Use for Female Urinary Incontinence

Wheelchair users require a quieter, more discreet version of the Suction Control Unit (1) (i.e. with concealed hoses). The Suction Control Unit (1) can be mounted to the person's wheelchair and the hoses concealed under the person's clothing. Many urinary incontinent adults are not in wheelchairs, but are bedridden. A larger urine collection bag (3) that does not contain super absorbent polymer can be attached to the Suction Control Unit (1) that can be emptied and reused. For ambulatory adults and children, a quiet Suction Control Unit (1) can be housed in a fanny pack that can also hold a concealed Urine Collection Bag (3).

Many urinary incontinent adults do not know in advance that they are about to urinate. It is therefore impractical to expect them to activate the Suction Control Unit (1) before urinating. Instead, a moisture sensor (55) is installed in the Female Pad (11) to automatically activate the Suction Control Unit (1) when moisture is sensed in the urine cavity (56).

Summary of Incontinent User Embodiments:

A quieter, more discreet version of the Suction Control Unit (1) for wheelchair users (i.e. with concealed hoses). The Suction Control Unit (1) could be mounted to the person's wheelchair and the suction hoses (13) concealed under the person's clothing. Many urinary incontinent adults are not in wheelchairs, but are bedridden. A larger urine collection bag (3) that does not contain super-absorbent polymer can be used that can be emptied by staff/care-givers and reused.

Many urinary incontinent adults do not know in advance that they are about to urinate. It is therefore impractical to expect them to activate the suction control unit (1) before urinating. Instead, a moisture sensor (55) can be installed in the Female Pad (11) and Male Cup (57) that will automatically activate the Suction Control Unit (1) when moisture is sensed in the urine cavity (56).

8. Most Preferred Embodiment—Disposable Power Source and Self Cleaning

Figure 9:
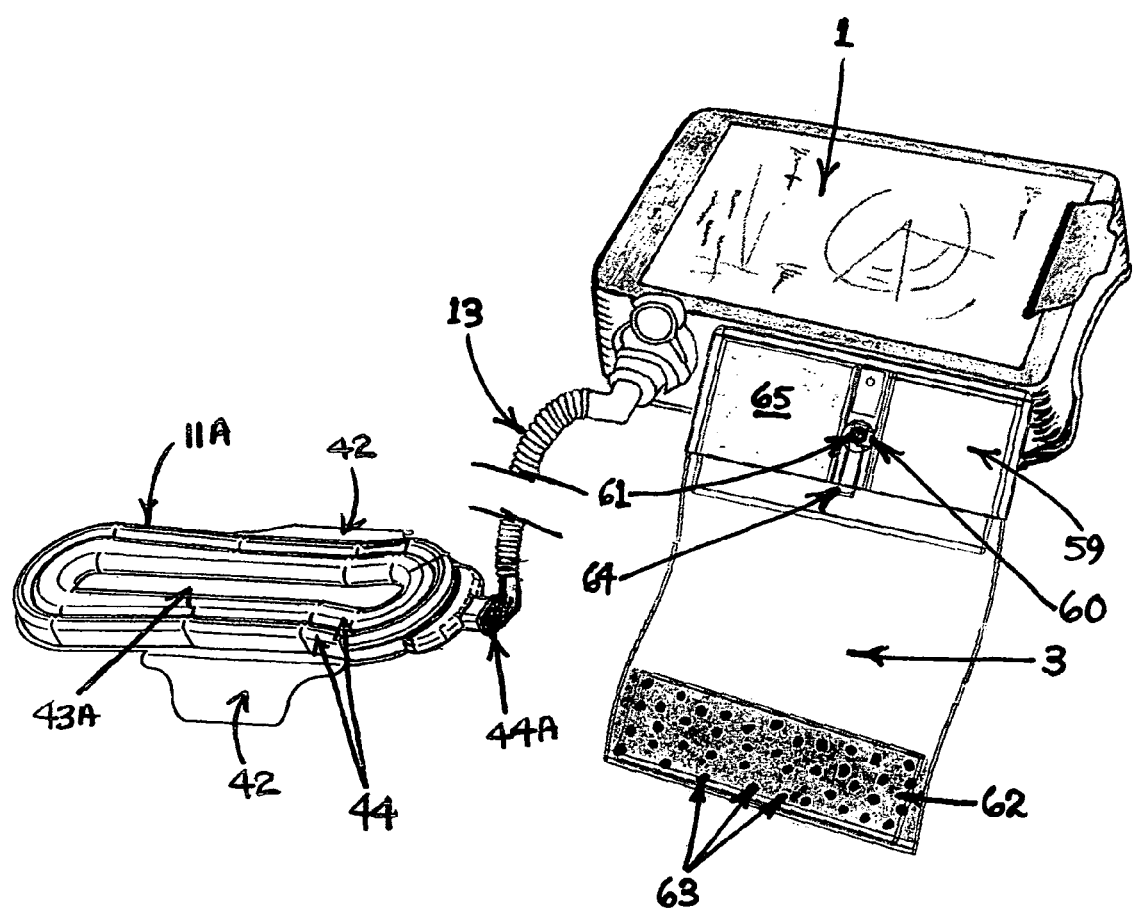
FIG. 9 is a perspective view of the female user self cleaning embodiment utilizing the fully inflated inflatable embodiment of the female pad with the urine and cleaning fluid storage bag attached.

The most preferred embodiment of the invention utilizes the Inflatable Urine Collection Means Embodiment as depicted in FIG. 9 wherein the urine collection means of the present invention is comprised of a Base Pad (43A) to which is attached at least one inflatable Air Cushion Tubing (44) that are inflated either automatically or by the user prior to urination by activation of the Air Pump (1A) that is housed inside Suction Control Unit (1).

Figure 8:
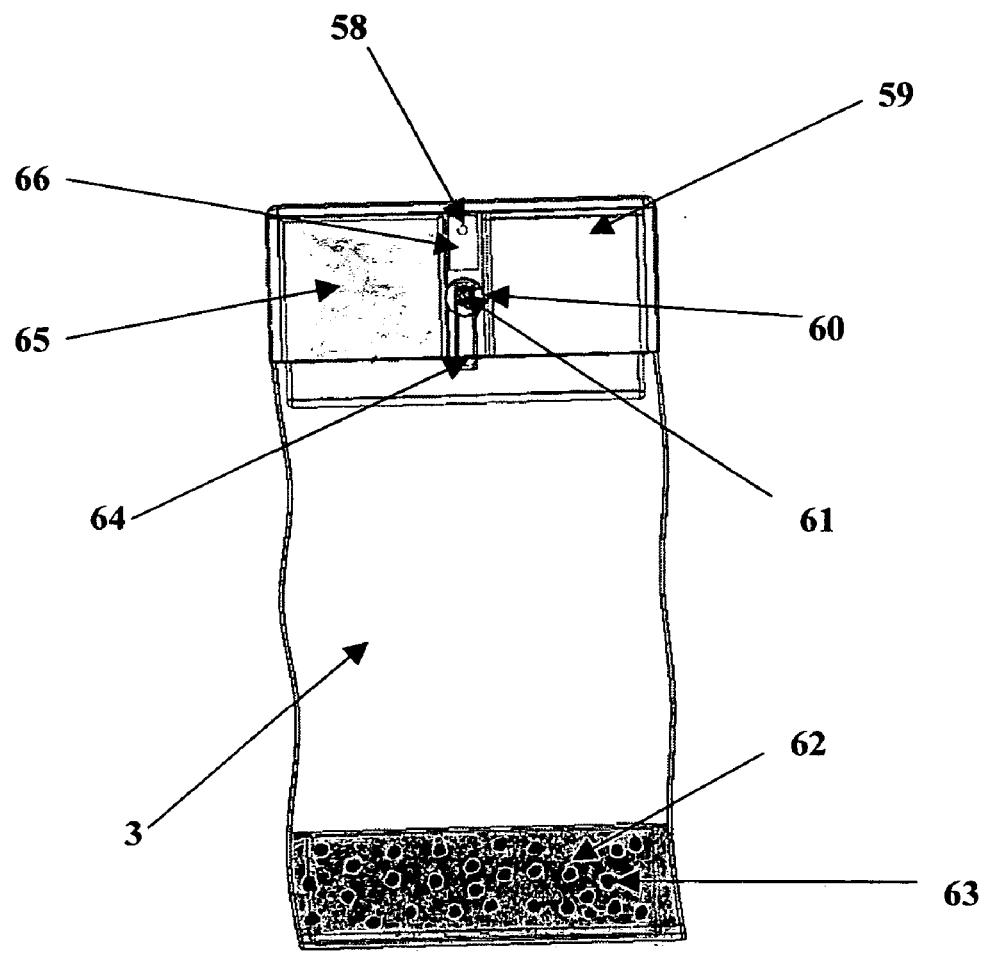
FIG. 8 is a perspective view of the urine and cleaning fluid storage bag of the self cleaning embodiment.

The Urine Collection Bag (3) in this embodiment provides four important functions for the invention; 1) it serves as a storage area for user discharged urine; 2) it serves as a power source for the invention having operatively attached thereto one or more disposable batteries; 3) it serves as a storage area for a cleaning fluid; and 4) it contains a gelling agent and a deodorizing agent to contain and control the user's discharged urine and any effluvia that it may produce. As depicted in FIGS. 8 & 9, the Urine Collection Bag (3) is attached to the Suction Control Unit (1) by means of a Quick Connect Fluid and Electrical Connection (61) which electrically connects the Urine Collection Bag (3) Disposable Battery Pack (65) to the Suction Control Unit (1) providing electrical current for all electrically operated components of the Suction Control Unit (1). The Quick Connect Fluid and Electrical Connection (61) also provides a leakproof connection to the Suction Control Unit (1) such that as fluids pass in and out of the Urine Collection Bag (3) do not leak from the invention. Once the invention is activated and a user is urinating, the Suction Control Unit (1) either by pumping or discharge from suction causes the urine to flow into the Urine Collection Bag (3) passing it through the Quick Connect Fluid and Electrical Connection (61) through the One Way Flow Valve Into the Urine Collection Bag (64) where the urine is then absorbed by the Super Absorbent Polymer Crystals (62) which urine is in turn deodorized by the Urine Deodorizer (63) that is mixed in with the Super Absorbent Polymer Crystals (62). Upon completion of urination, either manually or automatically, the Suction Control Unit (1) begins the cleaning process by reversing the pumping or suction direction thereby drawing a cleaning fluid from the Cleaning Fluid Compartment (59) of the Urine Collection Bag (3) through the One Way Cleaning Fluid Valve (60) into the Suction Control Unit (1) and ultimately back to the user thereby rinsing, cleaning and sanitizing the user and all parts of the invention not intended to store urine that have come in contact with the user's urine. Once the user and the invention are rinsed, cleaned and sanitized the pumping or suction action of the Suction Control Unit (1) is once again either manually or automatically reversed and the used cleaning fluid is then pumped or discharged from suction back into the Urine Collection Bag (3) passing it through the Quick Connect Fluid and Electrical Connection (61) through the One Way Flow Valve Into the Urine Collection Bag (64) where the used cleaning fluid is also absorbed by the Super Absorbent Polymer Crystals (62) which used cleaning fluid also is in turn deodorized by the Urine Deodorizer (63) that is mixed in with the Super Absorbent Polymer Crystals (62). Air pressure in the Urine Collection Bag (3) is regulated by the flow of air through the Air Exit Hole (58) and the effluvia is further controlled by causing the air that exits the Air Exit Hole (58) to first pass through a Charcoal Air Filter (66).

During urination the activated Air Pump (1A) pumps air into one or more Air Cushion Tubing (44) through the air hose portion of the Combined Suction and Air Pressure Hose (13A) and is connected by the Air Pressure Hose Connection (44A), which Air Cushion Tubing (44) when inflated forms an area where discharged urine from the user may pool without contact with the user and then be transported by suction through the suction hose portion of the Combined Suction and Air Pressure Hose (13A) by the vacuum suction airflow produced by the Suction Vacuum Pump (2) of the Suction Control Unit (1) that suck fluids and moisture out of the Inflatable Female Pad (11A) and away from the user's body. The Suction Control Unit (1) then transports the suctioned urine into the Urine Collection Bag (3) and the cleans the unit as stated above. After use and cleaning the Air Pump (1A) is deactivated and the Air Cushion Tubing (44)

deflates by means of compression brought on by the user's body weight after use returning the urine collection means to a flatter and more comfortable condition for the user. In its inflated condition the inflatable urine collection means provides a contained area for the pooling of the user's urine away from the body permitting the urine to be transported by the urine transport means and minimizing the opportunity for the urine to come in contact with the user's body or genital area. The Inflatable Female Pad (11A) has a contoured shape for a more comfortable and reliable fit. Stability Wings (42) attached to the sides of the Inflatable Female Pad (11A) serve to hold the Inflatable Female Pad (11A) in proper position on the user and prevent side leaks. The Inflatable Female Pad (11A) is held in place with a comfortable but sturdy undergarment available in women's apparel stores.

The Combination Suction and Air Pressure Hose (13A) at the front of the Inflatable Female Pad (11A) is connected to the Suction Control Unit (1). The Suction Control Unit (1) sucks all fluids from the Inflatable Female Pad (11A) through the Combination Suction and Air Pressure Hose (13A) and deposits them into the Urine Collection Bag (3). In this most preferred embodiment, the flexible, disposable Combination Suction and Air Pressure Hose (13A) is outfitted with a connection means on the end that connects to the Air Pressure Hose Connection (44A). The Combination Suction and Air Pressure Hose (13A) may be made of a convoluted, easily bendable material with spiral construction. This allows a smaller bending radius so that the Combination Suction and Air Pressure Hose (13A) can be stowed in a person's clothing or flight suit while not in use, and permits all of the urine to drain out of the Combination Suction and Air Pressure Hose (13A).

In this most preferred embodiment the Air Cushion Tubing (44) contains an open cell foam as a failsafe measure in the event of a failure of the Air Pump (1A), such that a user may slightly elevate their body allowing the Air Cushion Tubing (44) to decompress as the open cell foam takes on its decompressed shape and size once relieved of the user's seated body weight thereby forming an effective leak resistant urine collection or depository area for evacuation by the urine transport means when inflated.

While my above descriptions of the invention, its parts, and operations contains many specificities, these should not be construed as limitations on the scope of the invention, but rather as exemplifications of present embodiments thereof. Many other variations are possible, for example, other embodiments, shapes, and sizes of the device can be constructed to fit on a user and work with a unit designed to work by the principles of the present invention; various materials, pumps, colors and configurations can be employed in the unit's design that would provide interesting embodiment differences to users including such practical designs as would, for instance conceal the unit.

Accordingly, the scope of the invention should be determined not by the embodiments illustrated, but by the claims and their legal equivalents as filed herewith.

I claim:

1. An automatic bladder relief system comprised of:
   a urine depository means;
   a urine transport means attached to the urine depository means;
   a urine storage means attached to the urine transport means wherein the urine storage means is comprised of:
      a leakproof storage bag wherein the leakproof storage bag is comprised of a urine storage compartment and a cleaning fluid compartment;
   a disposable power source means;
   a cleaning means wherein the cleaning means is comprised of;
      a urination completion sensor capable of detecting the completion of a user's urination in the urine depository means;
      a cleaning fluid pump;
      a cleaning fluid contained in the cleaning fluid compartment; and
      a urination completion detection signal transmission means attached to the urination completion sensor and the cleaning means capable of activating the cleaning fluid pump by transmitting a signal thereto when the urination completion sensor detects the user's completion of urination, thereby pumping the cleaning fluid from the cleaning fluid compartment through the urine transport means to the urine depository means to the user and then to the urine storage compartment thereby cleaning away a user's residual urine from the automatic bladder relief system and depositing the user's residual urine and the pumped cleaning fluid in the urine storage compartment of the leakproof storage bag;
   the urine depository means is comprised of:
      a base pad;
      at least one air cushion tubing attached to the base pad; and
      an air pump attached to the air cushion tubing such that when the air pump is activated the air cushion tubing inflates from a generally flat condition to an inflated condition thereby forming with the base pad an area where urine discharged by a user can pool generally away from contact with the user's body and then the pooled urine can be transported by the transport means and upon deactivation of the air pump the air cushion tubing discharges the pumped air by means of compression caused by the user's seated body weight and returns to the generally flat condition.

2. An automatic bladder relief system comprised of:
   a urine depository means;
   a urine detection means attached to the urine depository means;
   a urine transport means attached to the urine depository means and the urine detection means wherein the urine transport means is activated to transport urine from the urine depository means by the urine detection means when urine is present in the urine depository means;
   a urine storage means attached to the urine transport means wherein the urine storage means is comprised of:
      a leakproof storage bag wherein the leakproof storage bag is comprised of a urine storage compartment and a cleaning fluid compartment;
   a disposable power source means;
   a cleaning means wherein the cleaning means is comprised of;
      a urination completion sensor capable of detecting the completion of a user's urination in the urine depository means;
      a cleaning fluid pump;
      a cleaning fluid contained in the cleaning fluid compartment; and a urination completion detection signal transmission means attached to the urination completion sensor and the cleaning means capable of activating the cleaning fluid pump by transmitting a signal thereto when the urination completion sensor detects the user's completion of urination, thereby pumping the cleaning fluid from the cleaning fluid compartment through the urine transport means to the urine depository means to the user and then to the urine storage compartment thereby cleaning away a user's residual urine from the automatic bladder relief system and depositing the user's residual urine and the pumped cleaning fluid in the urine storage compartment of the leakproof storage bag;

the urine depository means is comprised of:

a base pad;

at least one air cushion tubing attached to the base pad; and an air pump attached to the air cushion tubing such that when the air pump is activated the air cushion tubing inflates from a generally flat condition to an inflated condition thereby forming with the base pad an area where urine discharged by a user can pool generally away from contact with the user's body and then the pooled urine can be transported by the transport means and upon deactivation of the air pump the air cushion tubing discharges the pumped air by means of compression caused by the user's seated body weight and returns to the generally flat condition.

3. The automatic bladder relief system of claim 1 wherein the urine transport means is a fluid pump.

4. The automatic bladder relief system of claim 2 wherein the urine transport means is a fluid pump.

5. The automatic bladder relief system of claim 3 wherein the fluid pump further comprises the cleaning means wherein the pump also functions as a cleaning fluid pump.

6. The automatic bladder relief system of claim 4 wherein the fluid pump further comprises the cleaning means wherein the pump also functions as a cleaning fluid pump.

7. The automatic bladder relief system of claim 1 wherein the urine transport means is a suction pump.

8. The automatic bladder relief system of claim 2 wherein the urine transport means is a suction pump.

9. The automatic bladder relief system of claim 1 wherein the urine transport means is controlled manually by a user by the means of a switch.

10. The automatic bladder relief system of claim 2 wherein the urine detection means is comprised of:

a urine sensor capable of detecting the presence of a fluid in the urine depository means; and a urine detection signal transmission means attached to the urine sensor and the urine transport means activating the urine transport means by transmitting a signal thereto when the urine sensor detects the presence of the fluid.

11. The automatic bladder relief system of claim 1 wherein the leakproof storage bag is comprised of:

at least one air vent that allows only air to escape.

12. The automatic bladder relief system of claim 2 wherein the leakproof storage bag is comprised of:

at least one air vent that allows only air to escape.

13. The automatic bladder relief system of claim 11 wherein the leakproof storage bag contains absorbent polymer crystals.

14. The automatic bladder relief system of claim 12 wherein the leakproof storage bag contains absorbent polymer crystals.

15. The automatic bladder relief system of claim 1 wherein the urine transport means is powered by DC electrical current.

16. The automatic bladder relief system of claim 2 wherein the urine transport means is powered by DC electrical current.

17. The automatic bladder relief system of claim 1 wherein the urine transport means is powered by AC electrical current.

18. The automatic bladder relief system of claim 2 wherein the urine transport means is powered by AC electrical current.

19. The automatic bladder relief system of claim 11 wherein the disposable power source means is attached to the leakproof storage bag.

20. The automatic bladder relief system of claim 12 wherein the disposable power source means is attached to the leakproof storage bag.

21. The automatic bladder relief system of claim 19 wherein the disposable power source means is at least one disposable battery.

22. The automatic bladder relief system of claim 20 wherein the disposable power source means is at least one disposable battery.

23. The automatic bladder relief system of claim 1 wherein the air cushion tubing is also comprised of:

a foam insert of open cell composition which when placed under compression by the user's seated body weight allows the air cushion tubing to maintain a generally flat condition and the foam of open cell composition when relieved of the user's seated body weight causes the air cushion tubing to expand to a condition resembling the air cushion tubing inflated condition.

24. The automatic bladder relief system of claim 2 wherein the air cushion tubing is also comprised of:

a foam insert of open cell composition which when placed under compression by the user's seated body weight allows the air cushion tubing to maintain a generally flat condition and the foam of open cell composition when relieved of the user's seated body weight causes the air cushion tubing to expand to a condition resembling the air cushion tubing inflated condition.

* * * * *